United States Patent [19]
Kaster

[11] 3,959,827
[45] June 1, 1976

[54] HEART VALVE PROSTHESIS

[76] Inventor: Robert L. Kaster, 2730 Vagabond Lane, Wayzata, Minn. 55391

[22] Filed: July 30, 1974

[21] Appl. No.: 493,022

Related U.S. Application Data

[63] Continuation-in-part of Ser. No. 282,706, Aug. 8, 1972, Pat. No. 3,825,957.

[52] U.S. Cl. .................................. 3/1.5; 137/527; 137/527.4; 137/527.8; 251/65
[51] Int. Cl.² .......................................... A61F 1/22
[58] Field of Search .................... 3/1, DIG. 3, 1.5; 137/527, 527.4, 527.8; 251/65

[56] References Cited
UNITED STATES PATENTS

| | | | |
|---|---|---|---|
| 2,646,071 | 7/1953 | Wagner | 251/65 X |
| 3,370,305 | 2/1968 | Goott et al. | 3/1 |
| 3,409,038 | 11/1968 | Blackford | 251/65 X |
| 3,438,394 | 4/1969 | Nakib | 3/1 X |
| 3,451,067 | 6/1969 | Jordan | 3/1 |
| 3,476,143 | 11/1969 | Kaster | 3/1 X |
| 3,546,711 | 12/1970 | Bokros | 3/1 |
| 3,594,824 | 7/1971 | Nakib | 3/1 |
| 3,825,956 | 7/1974 | Child | 3/1 |

Primary Examiner—Ronald L. Frinks
Attorney, Agent, or Firm—Burd, Braddock & Bartz

[57] ABSTRACT

A heart valve having a base with a passage and a free-floating pivoting disc for controlling the flow of blood through the passage. Inwardly directed proximal and distal pivots control the pivoting movement of the disc. The pivots are offset from the diameter of the disc so that the disc pivots between its open and closed positions between its center and an outer peripheral edge of the disc. The disc is held in free-floating assembled relation with the pivots and base with a curved retaining rod having a curved end projected through a central hole in the disc. In one form of the valve a permanent magnet in the disc assists the closing of the disc in response to a drop in the pressure of blood moving through the valve passage. A suture collar surrounds and is mounted on the outer portions of the base. A low friction sleeve interposed between the base and the collar permits rotation of the valve relative to the suturing collar after the collar has been attached to the heart tissue.

27 Claims, 16 Drawing Figures

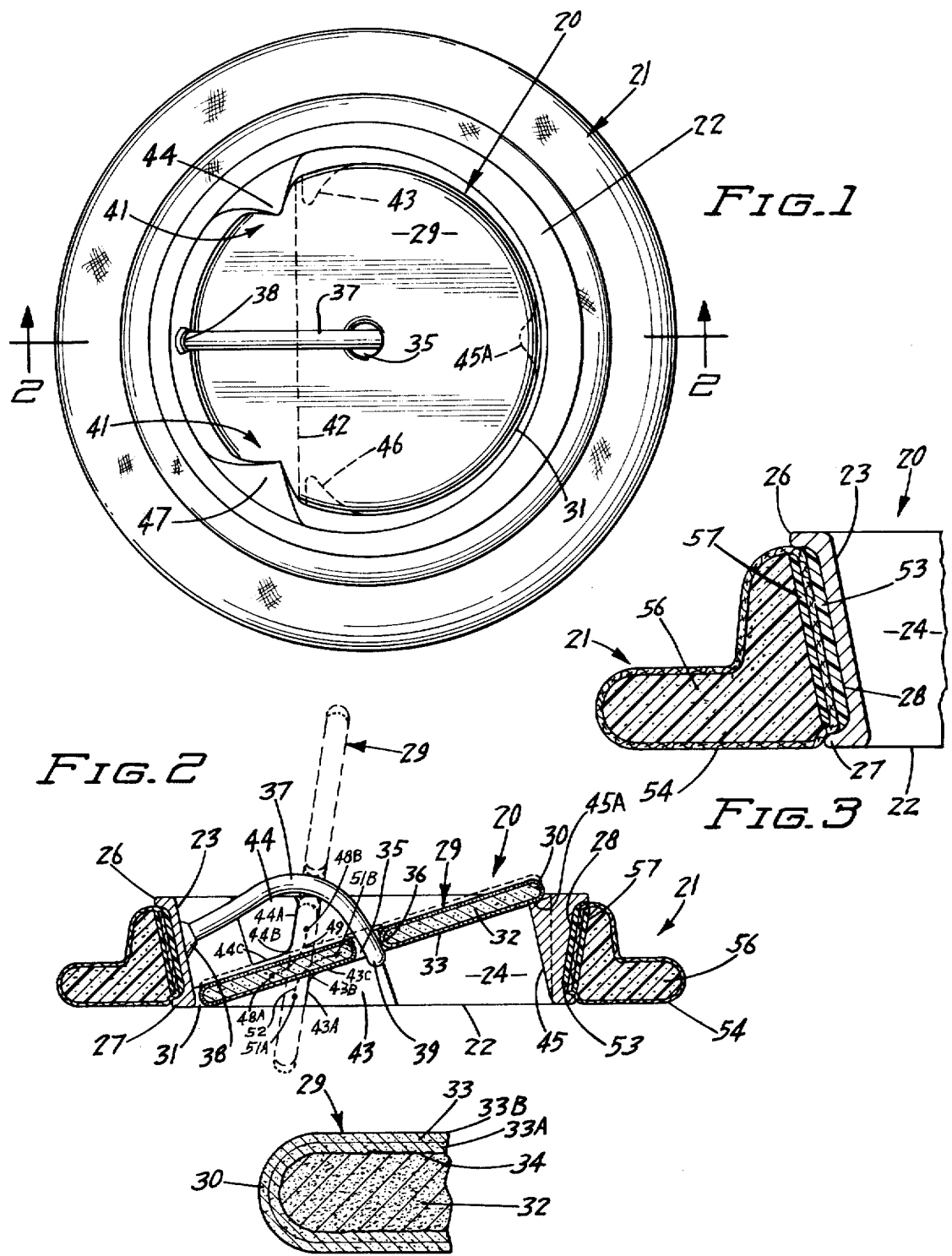

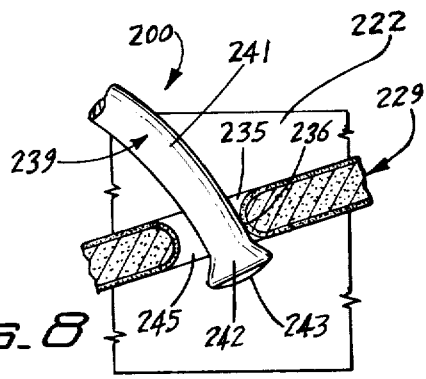
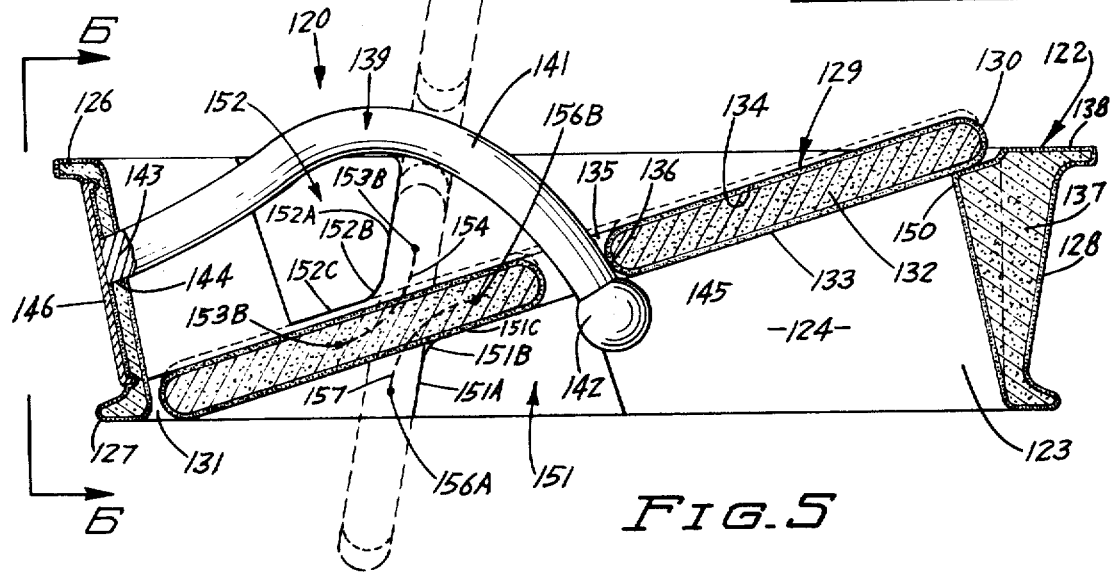
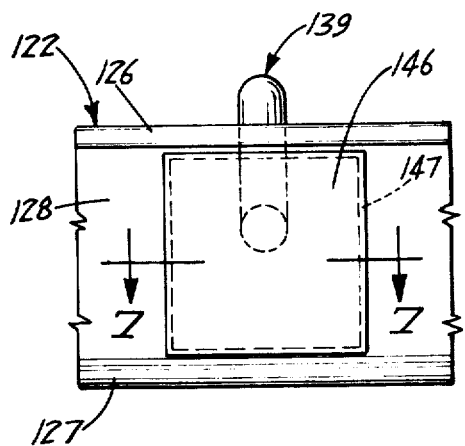
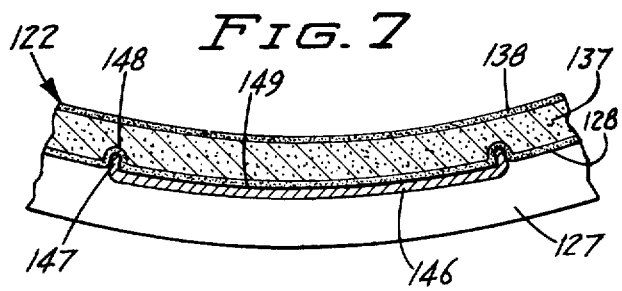

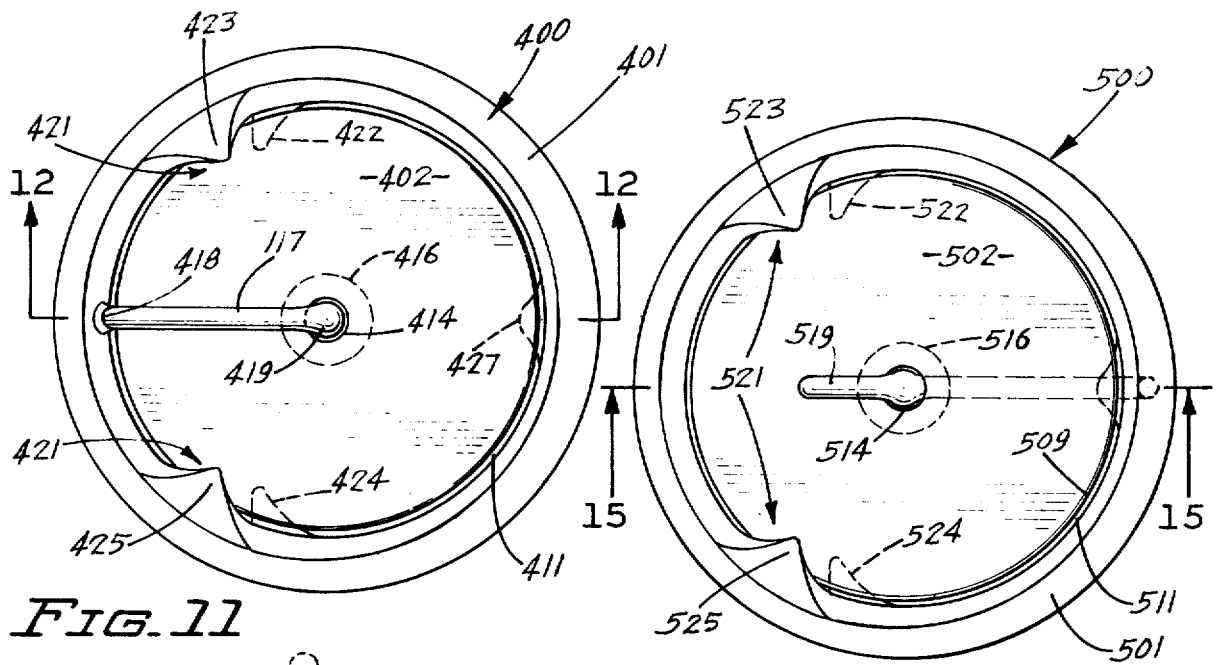
*Fig.11*
*Fig.14*
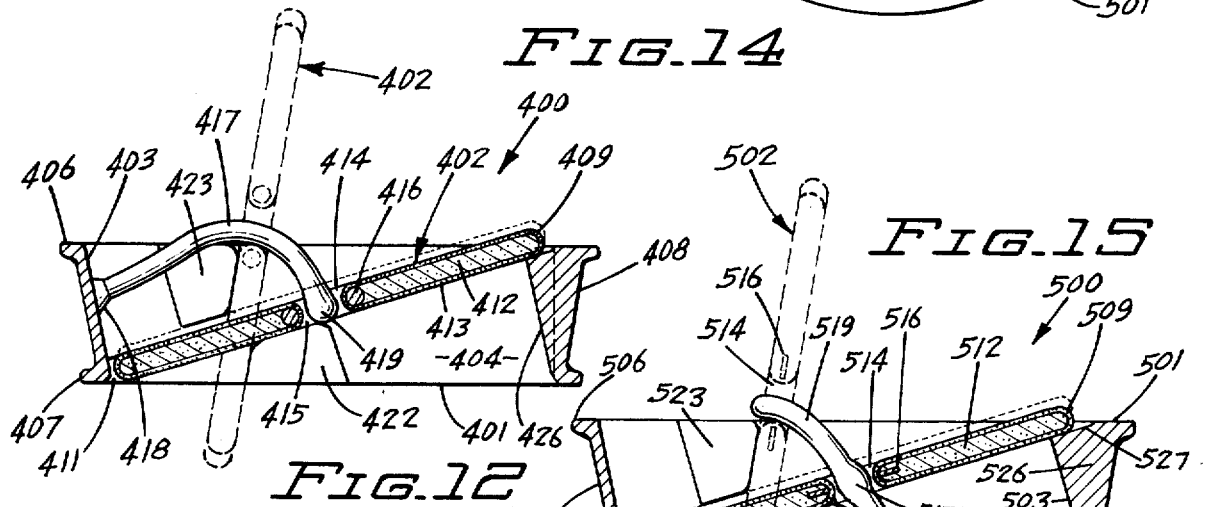
*Fig.12*
*Fig.15*
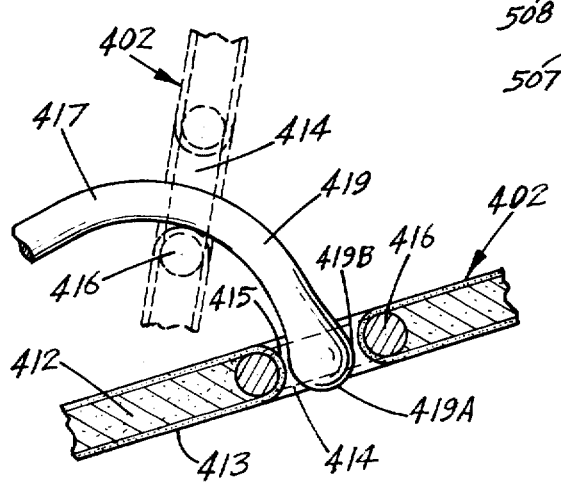
*Fig.13*
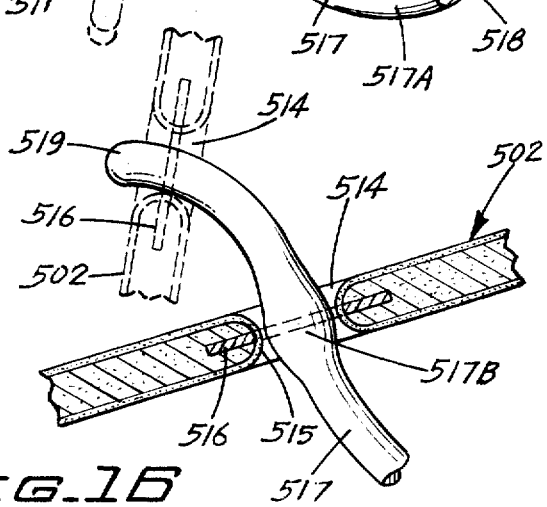
*Fig.16*

HEART VALVE PROSTHESIS

CROSS REFERENCE TO RELATED APPLICATION:

This application is a continuation-in-part of U.S. application Ser. No. 282,706, filed Aug. 8, 1972, now U.S. Pat. No. 3,825,957.

BACKGROUND OF INVENTION:

Heart valve prostheses are used in patients whose natural valves are damaged by conginital malformations or diseases and associated scarring and calcifications. Numerous heart valve designs have been developed using either a ball, leaflet or disc valving member. Each of these designs has certain advantages as well as deficiencies. They attempt, but do not achieve, the duplication of healthy natural heart valves. Problems of prosthetic heart valves are largely due to the shape and operating structure of the valves and the materials used in the valves.

Durability is a crucial factor in the clinical applicability of any heart valve, as a heart valve must open and close approximately forty million times a year. It is imperative that the material used in the heart valve be immune to biochemical degradation and mechanical failure due to wear and fatigue of rubbing or flexing of the components of the valve. Biodegration is interrelated with mechanical failure as it accelerates material fatigue and material breakdown. Rubbing and wear can accelerate the biochemical reaction, continually -exposing new surfaces to corroding media.

Leaf-type valves, as disclosed by Lord in U.S. Pat. No. 2,682,057 and Servelle in British Pat. No. 1,160,008, and disc-type valves as disclosed by Wada in U.S. Pat. No. 3,445,683; Schimert et al in U.S. Pat. No. 3,538,514 and Bokros in U.S. Pat. No. 3,546,711, have low pressure gradients and fair flow characteristics.

DeLaszlo, in U.S. Pat. No. 3,526,906, discloses prosthetic implants made from carbonaceous materials. The heart valve implant has a rigid base of carbon or graphite carrying a silicone rubber ball or a disc having legs of plastic material. Bokros, in U.S. Pat. No. 3,546,711, shows a carbon coated valve having a gate pivoted on a fixed pin. Cruz et al, in U.S. Pat. No. 3,367,364, and Kaster, in U.S. Pat. No. 3,467,143, disclose several pivoting disc heart valve designs. Shiley describes a pivoting disc heart valve in U.S. Pat. No. 3,698,018.

Nakib, in U.S. Pat. No. 3,438,394, discloses in FIGS. 8 and 9, a heart valve having a toroidal valving member that has a combined linear and angular movement as it opens and closes. Jordan, in U.S. Pat. No. 3,451,067, shows a heart valve having a check linearly guided on a rod. Similar valves are disclosed in U.S. Pat. Nos. 3,503,079; 3,601,877 and 3,812,542 as well as British Pat. No. 1,016,811. These valves, except the valves of Kaster and Shiley, are not pivoting disc valves. The base and disc pivoting structures of these valves are not adapted to be made entirely of rigid carbon materials. Parts of either the base or the pivoting structure must be movable or flexible to permit assembly of the disc into the base.

The natural heart valve has very little reverse flow of blood during the closing episode of the valve. The natural valve progressively closes in response to a drop in pressure of the blood flowing through the valve opening. Eddy currents on the distal side of the valve also effect the progressive closing of the valve. Artificial heart valves do not progressively close in response to a drop in the pressure of blood flowing through the valve passage.

Clinical use of pivoting disc valves wherein the valving member angularly moves to open and closed positions has shown that it is desirable to adjust the angular position of the valve after it has been implanted in the heart. The base of the valve is rotated relative to the suturing member secured to the heart tissue to orientate the valve member, as a pivoting disc, away from calcifications which can interfere with the free movement of the valving member. The valve is rotated with the handle or holder used to position the valve during the implant procedure. In order to permit angular orientation of the valve after it has been implanted, the suturing member has a loose fit on the valve base. This loose relationship between the suturing member and base is undesirable as the valve may shift in use and move or slide relative to the suturing member.

SUMMARY OF THE INVENTION

The invention broadly relates to a check valve for controlling the flow of fluid through a passage in a housing or ring. The invention is specifically directed to a heart valve prosthesis having a pivoting disc means movable between open and closed positions relative to a base to control the flow of blood through a passage in the base. The disc means located within the passage has an annular peripheral edge cooperating with an inside wall of the base to restrict the flow of blood through the passage when the disc means is in its closed position. A means secured to the base has a rod section extended through a central hole in the disc means to hold the disc means in free-floating relation with the base and guide the pivotal movement of the disc means. The disc means is free to rotate about its central axis as it pivots between the open and closed positions. Pivot means located on the base offset from a diameter of the passage are engageable with the disc means for controlling the pivotal movement of the disc means with the rod section offcenter from the diameter of the disc means. The pivot means includes members or legs engageable with separate proximal and distal portions of the disc means during movement of the disc means.

In one form of the valve of the invention the valving member has means, as a permanent magnet, to assist the closing of the valve member in response to a drop in the pressure of the blood moving through the valve passage. The valving member progressively closes as the pressure difference across the valve decreases.

A suturing collar is movably mounted on the valve base to permit rotation or circumferential orientation of the valve relative to the suturing collar. A low friction sleeve located between the suturing member and the outer wall of the valve base permits angular orientation of the valve after it has been implanted and still has a relatively firm relationship with the valve base.

In one form of the heart valve, the disc and base have coatings or outer skins of pyrolite carbon. The rod section is located adjacent the distal side of the disc and secured to the base. The rod section is curved and projects through a center hole in the disc means terminating in an end located adjacent the proximal side of the disc means when it is in its closed position.

Another form of the heart valve has a retaining rod located adjacent the proximal side of the base and extended through a hole in the valving disc.

IN THE DRAWINGS

FIG. 1 is a top plan view of a first heart valve in assembly relation with a suturing member of the invention;

FIG. 2 is a sectional view taken along the line 2—2 of FIG. 1;

FIG. 3 is an enlarged sectional view of the suturing member mounted on the base of the heart valve;

FIG. 4 is an enlarged fragmentary sectional view of an outer peripheral portion of the disc of the heart valve;

FIG. 5 is a sectional view similar to FIG. 2 of a second heart valve of the invention;

FIG. 6 is a fragmentary side elevational view taken along line 6—6 of FIG. 5;

FIG. 7 is an enlarged sectional view taken along lone 7—7 of FIG. 6;

FIG. 8 is a sectional view of the center section of a valve disc and retaining rod of a modification of the value shown in FIG. 5;

FIG. 11 is a top plan view of a fourth heart valve of the invention;

FIG. 12 is a sectional view taken along line 12—12 of FIG. 11;

FIG. 13 is an enlarged sectional view of a portion of FIG. 12;

FIG. 14 is a top plan view of a fifth heart valve of the invention;

FIG. 15 is a sectional view taken along line 15—15 of FIG. 14; and

FIG. 16 is an enlarged sectional view of a portion of FIG. 15.

Figure 9:
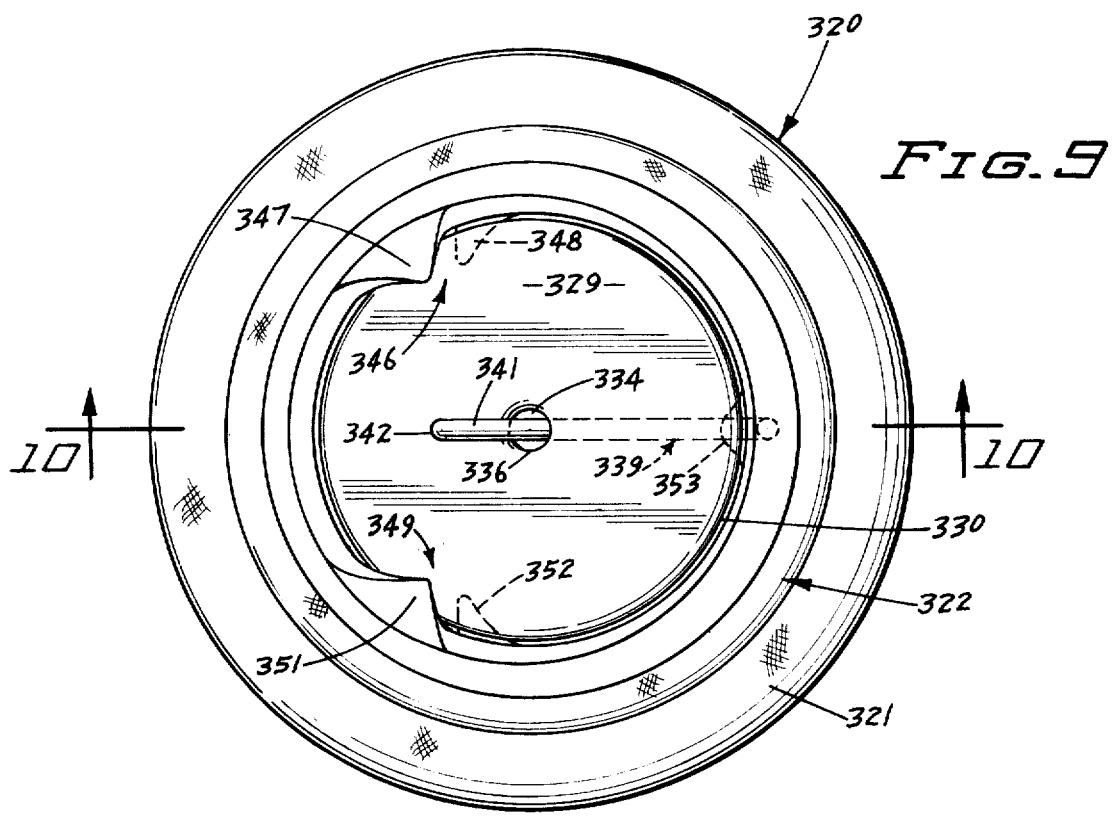
FIG. 9 is a third heart valve of the invention.

DESCRIPTION OF PREFERRED EMBODIMENTS:

Referring to the drawings, there is shown in FIGS. 1–4 a one-way valve, specifically a heart valve, adapted for use in the mitral position of a human heart. The valve, indicated generally at 20, is in assembled relation with a mitral suturing member or sewing ring indicated generally at 21. Valve 20 has a base or annular housing 22 associated with a movable valving member or disc 29. The housing 22 has an annular inner wall 23 defining a passage 24 through the valve. Extended outwardly from the upper or distal edge of housing 22 is an annular flange 26. A similar outwardly directed annular flange 27 is at the lower or proximal side of housing 22. Housing 22 has a cylindrical outer circumferential wall 28 located between flanges 26 and 27 for accommodating suturing member 21. Housing 22 can be a one-piece member including a metal, as titanium, a core or substrate covered with a pyrolite skin, a plastic member, or a ceramic member.

Valving member 29 is a generally flat disc having a circumferentially uninterrupted outer peripheral edge 30 which cooperates with the inner wall 23 to restrict reverse flow of blood through passage 24 when the disc is in the closed position. The outer peripheral edge 30 of the disc 29 is spaced from the inner wall 23 by a small annular space 31. Space 31 is of a size to permit limited reverse, or leakage, flow of blood through the passage 24 when the disc is in the closed position. Disc 29 is retained in free-floating rlationship on the base with a retaining means shown as a rod 37. Disc 29 is free to randomly rotate about its central axis as it angularly moves between its open and closed positions to control one-way movement of blood through the valve passage 24.

Referring to FIGS. 2 and 4, disc 29 has a core or substrate 32 that is entirely covered with a pyrolite carbon coating or skin 33. The skin is positively joined to the substrate by a bond 34. The substrate 32 is a polycrystalline graphite coated with a silicone alloyed pyrolite carbon skin 33. Substrate 32 may have a density less than the density of blood. Also, the substrate 32 can have a hollow chamber. Skin 33has a pyrolite carbon prime layer 33A covered with a pyrolite carbon finish layer 33B. Layers 33A and 33B are deposited separately at low temperatures. The thermal coefficient of expansion of the substrate graphite is such that during cooling after application of skin 33, the outer pyrolite carbon layer 33B is forced into a compressive state of stress. This enhances the toughness and wear characteristics of the skin 33. The pyrolite carbons are deposited on the substrate in a fluidized bed of hydrocarbon containing gaseous environment. These carbons are stronger and tougher than other bulk forms of carbons. The coatings can be applied to a variety of substrates including metal, ceramics and graphite. The substrates can have complex shapes and corners without danger of delaminating and cracking. The process of depositing pyrolite carbons in this manner is described in U.S. Pat. No. 3,579,645. Disc 29 can be made of other materials that are wear resistant and compatible with blood and body fluids and tissues. Examples of suitable materials are plastics, as polycarbonates, and alumina ceramics.

Disc 29 has a central hole 35 for accommodating the curved retainer element or rod 37. The outer or base end 38 of rod 37 is secured to the inside of housing 22 and projects upwardly and radially toward the center of passage 24. The free inner portion of rod 37 is curved downwardly generally along the pivotal arc or path of the angular movement of the disc 29 so that it has minimum interference with the pivoting of the disc. The inner end 39 of rod 37 projects through the center hole 35 of disc 29 when the disc is in the closed position. Rod 37 is slightly smaller in diameter than the diameter of hole 35 at all times. This diametric relationship between the rod and the hole also permits some movement or shifting of the disc in its flat plane as it opens and closes. Rod 37 has a cross sectional size smaller than the size of hole 35 in disc 29 whereby blood can flow through the hole.

As shown in FIG. 2, disc 29, when in the closed position, is inclined relative to a longitudinal axis of passage 24. This inclination is preferably 18° with respect to the horizontal. It is understood that other angles of inclination can be utilized. Disc 29 angularly moves from the closed position, as shown in broken lines, when there is an increase in the pressure of blood on the proximal side of the disc. When fully opened, the disc 29 is at a slight angle, preferably 75°–80°, with respect to the horizontal or transverse axis of passage 24 and is located laterally of the central longitudinal axis of the passage 24. This permits free central flow of blood through passage 24 while at the same time it allows the blood to flow on opposite sides of disc 29. The pivotal movement of disc 29 is controlled by pivot means indicated generally at 41 and rod 37 which provide the disc with an offcenter pivoting movement. The pivotal movement of disc 29 can be viewed with respect to a reference chord line 42. Chord line 42 is spaced from the center opening 35 and inwardly of the periphery of the disc at a point along the line which is parallel to the chord reference line 42.

Pivot means 41 comprise a first pair of pivots 43 and 44 directed inwardly into passage 24 and a second pair of pivots 46 and 47 directed generally toward the first pair of pivots and into passage 24. Each pair of pivots has a proximal pivot and a distal pivot, located on opposite sides of the disc, to accommodate a portion of the disc. The pairs of pivots are substantially identical in structure. The following description is limited to pivots 43 and 44, as shown in FIG. 2.

Pivot 43 has an inwardly directed leg, projection or element having a first generally upright surface or face 43A which merges into a curved corner 43B. The corner 43B joins to an upper inclined surface or face 43C that extends circumferentially toward the diameter of the base. Pivot 44 is a leg, projection, or element having a generally upright surface or face 44A which is generally parallel to face 43A. Face 44A merges with a round corner 44B. Corner 44B is joined to a lower inclined surface or face 44C. Face 44C extends away from the diameter of the disc. Corners 43B and 44B are spaced from each other a distance slightly greater than the thickness of disc 29 to provide for free pivoting and rotation of the disc relative to the pivots.

The inner wall of base 22 diametrically opposite rod 37 has a slight inwardly directed projection or stop 45 with an upper face 45A engageable with a portion of the disc when it is in the closed position, as shown in FIG. 2. Stop 45 functions in concert with the upper face of each of proximal pivots 43, 46 and the lower face of each distal pivot 44, 47 as a structure to limit the closed position of disc 29. When the disc is in the maximum open position, it engages the generally upright facs 43A and 44A of pivots 43, 44 and 46, 47 which serve as stops to limit the open position of disc 29, as shown in broken lines in FIG. 2.

Referring to FIG. 2, with disc 29 in the closed position, the disc will initially move up and then pivot around fulcrum corner 44B. Pivot axis 48A will follow the curved path 49 until the disc is in the full open position. At that time the pivot axis 48A will be at 48B adjacent the generally upright stop face 44A. The pivot axis 48 of the disc generally follows the curvature of the fulcrum surface. During opening of the disc, the pivot axis moves upwardly, or in the proximal direction and toward the center of the disc. This pivotal movement reduces the impact of disc 29 on the stop surfaces 43A and 44A of each pivot.

The reduction of pressure brought on the proximal side of the valve will close the disc 29. The disc 29 will initially drop a slight amount and pivot about the pivotal chord axis 51A. As the disc closes, the chord axis moves along the curved line 52 until the disc is closed. When the disc is closed, the pivotal axis is at 51B. During closing of the disc, the pivotal chord axis raises, or moves in the proximal direction, and shifts generally toward the center or diameter of the disc, thereby reducing the impact of the disc on the closed stop surfaces 43B, 44B and 45A. As the pivot axis shifts toward the diameter of the disc, the relative balancing weight of the disc in addition to the fluid acting on the distal surface of the disc will tend to balance the disc on the proximal pivots 43 and 46 and thereby reduce the closing momentum of the disc. During the opening and closing episodes of the disc, the chord pivot axis of the disc remains parallel to and is unaltered with respect to the chord reference axis 42.

The circumferentially spaced pairs of pivots 43, 44 and 46, 47 and rod 37 provide a coordinated triangular structure for retaining and controlling the movement of the disc 29. The triangular arrangement of structure enables disc 29 to have smooth movement between its open and closed positions and has a minimum of retardation of rotation of disc 29. The center and in-passage location of rod 37 gives the valve a low overall profile.

Referring to FIGS 2 and 3, suturing member 21 is located around the base 22 between the flanges 26 and 27. A sleeve 53 of plastic material having low friction characteristics, as Teflon or the like, is positioned adjacent cylindrical outer circumferential wall 28 of the base between flanges 26 and 27. The suturing member 21 comprises a fabric cover 54. Cover 54 is a biologically inert, porous material that is compatible with the chemicals and fluids of the body and does not deteriorate with time. The cover 54 can be interlaced or knitted fabric to provide a mesh or spaces into which the living tissue of the heart grows in the healing process. This forms a permanent union with the suturing member and living tissue independent of the sutures applied by the surgeon. The cover 54 can be made entirely of a synthetic fiber, as DuPont "Teflon" or "Dacron." Enclosed within cover 54 is a body or core of plastic material 56. The core of plastic material 56 has an outer or peripheral surface that is bonded to the inside surface of the cover 54 during the process of making the suturing member. Stitches (not shown) can be used to secure the ends of the cover 54 together to form a continuous tubular member that surrounds the core of plastic material 56. A cylindrical sleeve member or collar 57, of heat shrinkable plastic or like material, is used to uniformly hold a portion of the cover 54 in surface engagement with the sleeve 53. Cylindrical member 57 is heat shrunk to hold the suturing member in engagement with sleeve 53 with force sufficient to allow rotation of base 22 relative to suturing member 21 after the suturing member has been attached to the heart tissue. This allows the surgeon to orientate the position of the heart valve in the heart after it has been implanted to avoid any obstructions that may interfere with the proper functioning of valve disc 29.

Core material 56 is preferably a pliable plastic material, as Dow-Corning "Silastic", fluorosilicone rubber, or a similar synthetic resinous plastic material that is compatible with human tissues and body fluids. In addition, core material 56 is sterilizable, biologically inert, non-irritating and nontoxic to body tissues and body fluids. On heat curing the plastic core material 56, a uniform bond is achieved between the outer peripheral surface of the core material and the inside surface of cover 54. This eliminates any pockets or separations between the cover and the core material which collect blood and other body fluids. Core material 56 cures at a relatively low temperature to a semi-rigid, relatively non-elastic plastic which retains its molded shape. During curing of core material 56, the heat will cause the collar 57 to uniformly shrink in diameter so that it will hold the cover in light frictional engagement with uniform circumferential force on sleeve 53. The process of forming the suturing member on the base of a heart valve does not form a part of this invention. The suturing member can also be the suturing member disclosed in U.S. Pat. No. 3,781,969.

Referring to FIG. 5, there is shown the second heart valve of the invention, indicated generally at 120. The valve 120 has a base or annular housing 122 and movable valving member or disc 129. Housing 122 has an annular inner wall 123 defining a passage or opening 124 through the housing whereby blood can flow through the passage. The valving disc 129 functions to permit one-way flow of blood through the passage 124 and restrict the flow of blood through the passage 124 in the opposite direction.

Extended outwardly from the upper or distal edge of the housing 122 is an annular flange 126. The lower or proximal side of housing 122 has a similar outwardly directed flange 127. A cylindrical outer circumferential wall 128 is located between the flanges 126 and 127 for accommodating an annular suturing member or sewing ring (not shown).

The valving member or occluder 129 is a generally flat disc having a circumferentially uninterrupted outer peripheral edge 130 which cooperates with portions of the inner wall 123 to limit or restrict reverse flow of blood through the passage 124 when the disc is in the closed position. The other peripheral edge 130 of the disc 129 is slightly spaced from the inner wall 123 by an annular space 131. Space 131 is of a size to permit limited reverse, or retrograde, flow of blood through the passage 124 when the disc 129 is in the closed position, as shown in full lines in FIG. 5.

The disc 129 has a core or substrate 132 that is entirely covered with a coating or skin 133. Preferably, skin 133 is of a silicone-alloyed pyrolite carbon material. The skin can have a plurality of layers, as shown in FIG. 4. The substrate 132 can be any rigid material, as metal, plastic, carbon or the like. The substrate can contain a hollow chamber to reduce its weight. The skin 133 is attached to the outer surface of the substrate with a bond 134 in the process of applying the skin 133 to the substrate 132.

Disc 129 has a hole 135 in the center portion thereof. The inner annular wall 136 surrounding the hole 136 has a semicircular cross sectional shape.

Housing 122 has a substrate 137 entirely covered with a skin or coating 138. Preferably, the skin 138 is of a siliconealloyed pyrolite carbon material having a plurality of layers similar to skin 33 shown in FIG. 4. Housing 122 can be made of any suitable materials including plastics, metals or ceramics.

Disc 129 is retained in free floating relationship on the base 122. The disc 129 is free to rotate about its central axis 360° as it angularly moves between its open and closed positions to control the one-way movement of blood through passage 124. A retainer, indicated generally at 139, is fixed to the housing and serves to maintain the disc in free floating assembled relation with the housing. The retainer 139 is an elongated rod having an inwardly directed, downwardly curved outer section 141 terminating in a generally spherical end 142. Section 141 has an arcuate shape that generally follows the path of angular movement of the inner wall 136 of disc 129. The end 142 has a diameter slightly smaller than the diameter of the hole 135 and is lcoated on the proximal side of the disc 129. When disc 129 is in the closed position, the upper portion of end 142 extends a slight distance into hole 135. End 142 restricts the size of space 145 between the retainer and the disc 129 when the disc is in the closed position.

The outer end 143 of the retainer 139 projects through a hole 144 in housing 122. A rectangular plate 146, shown in FIGS. 6 and 7, secured to the outer end 143, fixes the position of retainer 139 on base 122. As shown in FIG. 7, plate 146 has an inwardly directed peripheral rib 147. Rib 147 extends into a groove 148 in the outer wall 128. An adhesive or bonding material 149 secures the plate 146 to the outer wall 128 so that the plate and wall have a substantially continuous outer surface.

The pivotal movement of the disc 129 is controlled with pivot means which provide the disc with an off-center pivoting movement. The disc pivots between its outer edge and its diameter between an open position and a closed position. The pivot means comprise first snd second pairs of pivots similar to pivots 43, 46 and 44, 47 shown in FIG. 1. Pivots 151 and 152, projected into the passage 124, are one pair of pivots. An identical pair of pivots projected into passage 124 generally toward the first pair of pivots is located on the opposite portion of the base in a manner as shown in FIG. 1. The pairs of pivots are located off-center or in eccentric locations relative to a diameter of the passage 124 whereby the disc 129 pivots about an off-center or eccentric axis as it opens and closes. The following description is limited to pivots 151 and 152.

Pivot 151 is a proximal pivot. Pivot 151 has a pivoting or fulcrum surface comprising a generally upright inclined side face 151A joined to a curved corner 151B and a top face 151C. Pivot 152 is a distal pivot. Pivot 152 has an upwardly inclined side face 152A extended downwardly to a curved corner 152B which extends to a bottom inclined face 152C. The pivots 151 and 152 are inwardly directed legs, elements or projections which have pivoting or fulcrum surfaces for controlling the arcuate movement of disc 129.

Housing 122 has an inwardly directed abutment or stop 150 located generally diametrically opposite the retainer 139. The stop 150 projects inwardly into the passage 124 and has an upper face engageable with a portion of the disc 129 when the disc is in the closed position. When the disc 129 is in the closed position, it is inclined relative to the longitudinal axis of the passage 124. This inclination preferably is 18° with respect to the horizontal. It is understood that other angles of inclination can be utilized for disc 129 when it is in the closed position. Disc 129 rests on the proximal pivot surfaces 151C of the proximal pivots and the stop 150 when it is in the closed position. Disc 129 angularly moves from the closed position to the open position, as shown in broken lines in FIG. 5, in response to an increase in the pressure of the blood on the proximal side of the disc. When fully opened, the disc 129 is at a slight angle, preferably 75°–80°, with respect to the longitudinal axis of the passage and is located laterally of the central longitudinal axis of passage 124. This permits the free central flow of blood through passage 124, while at the same time it allows the blood to flow on opposite sides of the disc. The open position of the disc is determined by side faces 151A and 152A of the proximal and distal pivots 151 and 152. The opposite portions of the disc 129 engage the side faces of the pivots to limit the opening pivotal motion of the disc.

When the disc 129 is in the closed position, it will initially move up and then pivot around fulcrum corner 152B. The pivot axis 153A will follow the curved path 154 until the disc 129 is in the full open position. At the time, the pivot axis 153A will be at 153B, adjacent the generally upright stop side face 152A. The pivot axis 153A generally follows the curvature of the fulcrum surface of th distal pivots and moves upwardly in the distal direction and toward the diameter of the disc. This pivotal movement of the disc 129 reduces the impact of the disc on the stop faces 151A and 152A of each pivot. The retainer 139 holds the disc 129 in assembled relation with the base 122 with portions of the disc located between the proximal and distal pivots. The disc 129 is free to rotate on the retainer 139 as the rod section 141 is smaller in diameter than hole 135 in the disc 129 and has a curvature that generally follows the curvature of the path of movement of the inner wall 136 of the disc 129.

Reduction in the pressure of blood on the proximal side of the disc 129 will cause the disc 129 to pivot to the closed position. Disc 129 will initially drop a slight amount and pivot about a pivot chord or off-center axis 156A. As disc 129 closes, the chord axis moves along the curved line 157 until the disc is closed. When the disc is closed, the pivot axis is at 156B. During the closing of the disc, the pivotal chord axis raises or moves in the distal direction and shifts generally toward the center or diameter of the disc. This reduces the amount of impact of the disc 129 on the closing stop 150 and proximal pivot surfaces 151C. As the pivot axis of the disc shifts toward the diameter of the disc, the weight of the disc in addition to the fluid acting on the distal surface of the disc will tend to balance the disc on the proximal pivot 151 and its associate proximal pivot and thereby reduce the closing momentum of the disc.

During the closing and opening episodes of the disc 129, the chord pivotal axis of the disc remains parallel to and is unaltered with respect to a chord reference line or axis that is parallel to the diameter of the disc.

Referring to FIG. 8, there is shown a modification of the end of the retainer of a heart valve, indicated generally at 200. The valve base 222 pivotally carries a disc 229 having a center hole 235. A circular, rounded inner wall 236 surrounds the hole 235. The retainer rod 239 has a curved portion 241 terminating in an end 242. The end 242 is generally cone-shaped and has a convex end 243. The cone shape of the end 242 provides a generally uniform space 245 between the rod end 241 and the wall 236 of the disc 229. The remaining structure of the valve 200 is identical to the structure of the valve shown in FIG. 5.

Figure 10:
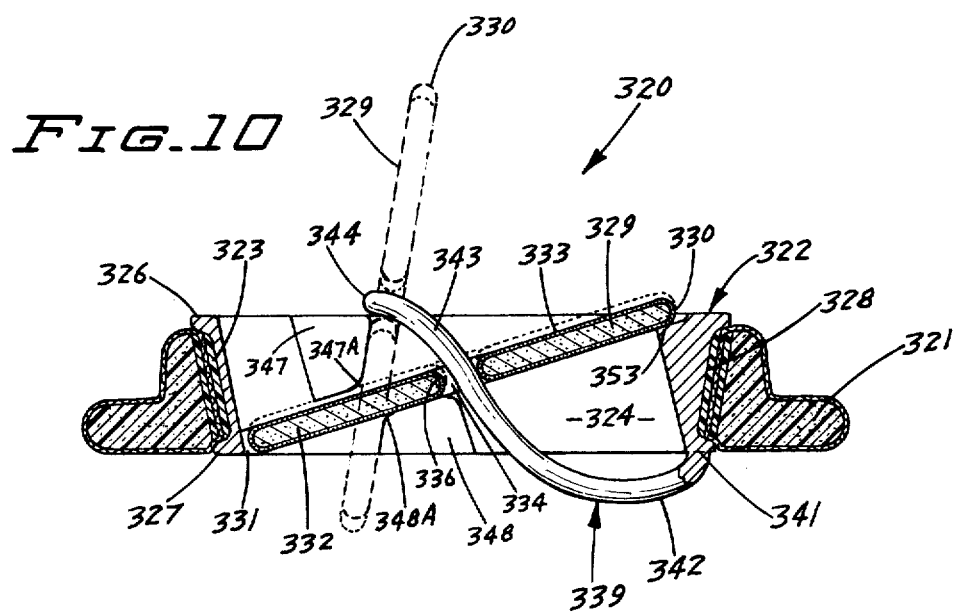
FIG. 10 is a sectional view taken along line 9—9 of FIG. 9.

Referring to FIGS. 9 and 10, there is shown the third heart valve of this invention indicated generally at 320 in assembled relation with an annular suturing member 321. Valve 320 has a base or annular housing 322 accommodating a movable valving member or disc 329. Base 322 can be a one-piece member including a metal, as titanium, a core or substrate covered with a pyrolite skin, a plastic or a ceramic.

Base 322 has a generally cylindrical annular inner wall 323 defining a passage or opening 324 permitting the flow of blood through the valve. A valving disc 329 is movably positioned within passage 324 to permit one-way flow of blood through the passage and restrict the flow of blood through passage 324 in the reverse or opposite direction.

Base 322 has a proximal annular flange 326 and distal annular flange 327. A cylindrical outside wall 328 extends between the flanges 326 and 327. The suturing member 321 is mounted on the wall 328. Suturing member 321 is the same construction as suturing member 21 shown in FIG. 3. Other types of suturing members can be mounted on base 322, such as the suturing member shown in U.S. Pat. No. 3,781,969.

Valving disc 329 is a generally flat, circular member having a circumferentially uninterrupted outer peripheral edge 330. Edge 330 cooperates with portions of inner wall 323 to restrict or limit reverse flow of blood through passage 324 when the disc is in the closed position, as shown in full lines in FIG. 10. Disc 329 is free to randomly rotate about its central axis, thereby eliminating localized sites of wear and fatigue and avoiding isolated breakdown of the valve structure. The diameter of disc 329 is such that the outer peripheral edge is spaced slightly inwardly from the inner wall 323 by annular space 331. Space 331 is of a size to permit annular limited reverse or retrograde flow of blood through passage 324 when disc 329 is in the closed position. The blood flows between the outer peripheral edge 330 and the inner wall 323 so as to wash the disc and wall surfaces to prevent clot formation and eliminate regions of blood stagnation.

Disc 329 has a core or substrate 332 that is entirely covered with a coat or skin 333. Skin 3 is a hard, wear-resistant material that is biologically inert and compatible with the material of base 322. Preferably, skin 333 is a silicone alloyed carbon material, as pyrolite carbon. Skin 333 can have a plurality of layers, as shown in FIG. 4. Substrate 332 can be any rigid mateiral, as metal, plastic, carbon or the like. The substrate can have a hollow chamber or chambers to reduce its weight. Disc 329 can be made of other materials that are wear-resistant and compatible with blood and body fluids and tissues. Examples of suitable materials are plastics, as polycarbonates, and alumina ceramics.

The center portion of disc 329 has a central hole 334. Hole 334 is defined by an inner annular wall 336. The cross sectional shape of wall 336 is a semi-circular configuration whereby the wall 336 does not have any abrupt projections or edges that can interfere with the flow of blood through hole 334 or collect blood tissue.

Disc 329 is movably positioned in free-floating relationship with the passage 324 of base 322 with a retainer indicated generally at 339. Disc 329 has limited axial movement, as shown in dotted lines in FIG. 10; has limited lateral movement, as shown in broken lines in FIG. 10; and is free to randomly rotate 360° about its central axis as it angularly moves between its open and closed positions. The open position is shown in broken lines in FIG. 10. Retainer 339 is an elongated radially inwardly projected rod extended from a proximal base portion 341 through the central hole 334 of disc 329. Retainer 339 has a generally broad "S" or reversed curve shape and is secured to the lower or proximal portion 341 of base 322. Preferably, retainer 339 is an integral part of base 322 that has been cured to the shape as shown in FIG. 10. Retainer 339 has a first section 342 extended downwardly and then curved inwardly below the lower or proximal plane of the lower edge of base 322 to locate section 342 outside of passage 324. A second section 343 projects generally upwardly thorugh the passage in the direction of the flow of blood or distal direction and terminates in a rounded end 344. Sections 342 and 343 have a smooth circular rod shape and are continuous to avoid any pockets or structure on which blood tissues can accumulate. Section 343 has an arcuate shape that generally follows the path of angular movement of the center portion of disc 329 as the disc pivots between its open and closed positions. Section 343 has a circular cross section and a diameter slightly smaller than the diameter of hole 334, thereby allowing a limited amount of blood to flow through the hole at all times and permitting the disc to have limited lateral movement as it pivots between its open and closed positions.

As shown in FIGS. 9 and 10, disc 329 has an off-center pivotal movement so that when the disc is in the open position, the blood has unrestricted centralized flow through passage 324. The blood flows adjacent opposite side surfaces of disc 329, thereby washing both side surfaces of the disc. Disc 329 pivots in a chordal region located between its outer peripheral edge and its diameter. Pivot means comprising a first pair of pivots indicated generally at 346 and a second pair of pivots indicated generally at 249 cooperate with the retainer 339 to restrict the movements of the disc as it moves between its open and closed positions. The first pair of pivots includes a proximal pivot 348 extended adjacent a portion of the proximal side of disc 329 and a distal pivot 347. Pivots 347 and 348 are integral with base 322 and extend a short distance into passage 324. Pivots 347 and 348 have fulcrum surfaces 347A and 348A respectively. Pivots 351 and 352 have similar fulcrum surfaces. Pivots 347 and 348 are projections, elements or legs that are spaced from each other a distance slightly greater than the thickness of the disc 329. The second pair of pivots 349 are circumferentially spaced from the first pair of pivots and extend into passage 324. The second pair of pivots comprise a distal pivot 351 and a proximal pivot 352. Pivots 351 and 352 are located adjacent opposite sides of the disc and are integral with base 322. Pivots 351 and 352 are projections, elements or legs spaced from each other and extended generally toward the first pair of pivots 346. The pairs of pivots 346 and 349 are located off-center or in eccentric locations relative to the diamter of passage 324 whereby disc 329 pivots about an off-center or eccentric axis as it opens and closes. The pivotal axis of disc 329 generally follows a chordal region of the passage 324 and can shift relative to the diameter of the passage as disc 329 opens and closes. In other words, the limited lateral movement of the disc allowed by the size of hole 334 relative to the diameter of retainer rod 339 permits the pivoting axis of the disc to have lateral transitory movement during the valving action of the disc. The offset pivotal axis of the disc remains generally parallel to a diameter of the disc whereby the disc has relatively smooth opening and closing movements.

Base 322 has an inwardly directed abutment or stop 353 located in general vertical alignment with the base portion 341. Stop 353 projects inwardly into the passage and has an upper face engageable with a portion of the disc 329 when the disc is in the closed position. As shown in FIG. 10, when disc 329 is in the closed position, it is inclined relative to the longitudinal axis of passage 324. Preferably, the inclination is 18° with respect to a horizontal plane of base 322. It is understood that other angles of inclination can be used for disc 329 when it is in the closed position. Being inclined, the closed disc 329 has a limited amount of angular travel or movement between its open and closed positions. This limited amount of travel eliminates intra-orifice obstruction to flow and also minimizes regurgitation of the blood through the valve passage. When fully open, as shown in broken lines in FIG. 10, disc 329 is at a slight angle, preferably 75°–80° with respect to the longitudinal axis of the passage 324 and is located laterally of the central longitudinal axis of the passage. This produces streamlined unrestricted centralized flow of blood through the passage.

In use, with disc 329 in the closed position as shown in full lines in FIG. 10, it will initially move upwardly or axially to the dotted line position until the distal or upper surface of the disc contacts the distal pivots 347 and 351. Disc 329 will then move around pivot fulcrum surfaces 347A of pivots 347 and 351 an off-center axis. Disc 329 will generally follow the curvature of retainer section 343 until the disc is in the full open position. The disc 329 moves laterally upwardly with the flowing blood, indicated by broken lines in the open position of disc 329 in FIG. 10. When the disc is in the full open position, opposite portions engage the proximal and distal pivots which limit the open position of the disc to a slight incline relative to the longitudinal axis of passage 324. During the opening of the disc it is free to randomly rotate 360° about its central axis.

A reduction in pressure of the blood on the proximal side of the disc will cause the disc to initially drop a slight amount and move about proximal pivots 348 and 352, rolling over the fulcrum surfaces 348A of pivots 348 and 352 to its fully closed position shown in full lines in FIG. 10. During the opening and closing episodes of the disc, the pivotal axis of the disc remains parallel to the reference diameter of the disc. The reference diameter of the disc is normal to the section line 10—10 of FIG. 9.

The retainer rods 37, 139 and 339 of the valves shown in FIGS. 2, 5 and 10, respectively, can be used without the associated pivots on the bases to control the pivoting movements of the valving discs. The rods serve as guides for the discs and maintain the discs in free floating relationship within the passages of the bases.

Referring to FIGS. 11 and 12, there is shown the fourth heart valve of the invention indicated generally at 400. Valve 400 has a rigid base or annular housing 401 made of metal, such as titanium, or a graphite substrate covered with pyrolytic carbon, ceramic material, and the like. Base 401 has an inner annular wall 403 defining a passage 404 through the base. A movable valving member 402 is operable to control the flow of blood through passage 404. Base 401 has an upper annular flange 406 and a lower annular flange 407. The flanges 406 and 407 extend laterally in an outward direction and define with an outer circumferential wall 408 a circular channel or groove for accommodating the suturing member (not shown). The suturing member may be the suturing member 21 shown in FIG. 2 or the suturing member shown in U.S. Pat. No. 3,781,969.

Valving member 402 is a disc having a generally flat, circular configuration and a circumferentially uninterrupted outer peripheral edge 409. Edge 409 cooperates with the inner wall 403 to restrict reverse or leakage flow of blood through passage 404 when the disc is in the closed position. The outer peripheral edge 409 is spaced from the inner wall by a small annular space 411. Space 411 is of a size to permit limited reverse or leakage flow of blood through the passage 404 when the disc 402 is in the closed position. The blood flows between the outer edge 409, the adjacent inner wall of the base and pivot means 421 to wash the base and disc surfaces and provide for continuous movement of the blood, thereby minimizing clot formation and regions of blood stagnation.

Disc 402 is retained in a free-floating relationship relative to the base 401 with retaining means shown as rod 417 and pivot means indicated generally at 421. The free-floating relationship of the disc 402 enables the disc to randomly rotate about its central axis as it angularly moves between its open and closed positions to control one-way movement of blood through the passage 404.

Referring to FIG. 12, disc 402 has a core or substrate 412 covered with a pyrolytic carbon coating or skin 413. The structure of the disc 402 is the same as the disc 29 shown in FIGS. 2 and 4. Disc 402 has a center hole 414 defined by a circular wall 415 having a smooth, semi-circular cross section. A toroidal or annular magnetic member 416 is embedded in the disc adjacent the circular wall 415. The magnetic member 416 is a permanent magnet. The permanent magnet can be steel, aluminum, nickel and cobalt alloys, or micropowder. Magnetic member 416 is located under skin 413.

A curved element or rod 417 attached to the base 401 extends through the hole 414 in disc 402. Rod 417 has an outer end 418 secured to a midportion of the base 401. Rod 417 projects radially toward the center of the passage 404 and has an enlarged free end 419. As shown in FIG. 13, end 419 has a generally bulbular shape. The terminal portion 419A of the end 419 is semi-spherical in shape and joined to a larger annular portion 419B. When the disc 402 is in the closed position, the annular portion 419B is in close proximity to the circular wall 415 of the disc. the magnet 416 has a magnetic force sufficient to attract it to the rod end 419, thereby establishing a force which urges the disc 402 to the closed position. Rod 417 from the end portion 419 is smaller in diameter than the diameter of the hole 414. This diametric relationship between the diameter of the rod 417 and the diameter of the hole 414 permits some movement or shifting of the disc in its flat plane as it opens and closes. Magnet 416 has less attraction to the smaller diameter section of rod 417 so the magnet urges the disc 402 to its closed position. Thus, when there is a drop in the pressure of blood flowing through the valve passage 404, magnet 416 will begin to move disc 402 to the closed position. In other words, when the flow of blood through passage 404 decreases, the magnet will start the disc 402 moving to its closed position.

The pivot means indicated generally at 421 include a first pair of pivots 422 and 423 directed inwardly into passage 404 and a second pair of pivots 424 and 425 directed generally toward the first pair of pivots and into passage 404. Each pair of pivots has a proximal or in-flow side pivot and a distal or out-flow side pivot. The proximal and distal pivots are located on opposite sides of the disc and accommodate portions of the disc 402. The pairs of pivots 422, 423 and 424, 425 are identical in structure and are identical to the pivots 43 and 44 shown in FIG. 2 and described hereinbefore.

The inner wall of base 401 diametrically oposite rod 417 has a slight inwardly directed projection or stop 426. The top of stop 426 has a face 427 engageable with a portion of disc 402 when the disc is in the closed position shown in FIG. 12. Stop 426 functions in concert with the upper faces of the proximal pivots and the lower faces of the distal pivots to limit the closed position of the disc 402. When disc 402 is in the closed position, it is at an inclination of preferably 18° with respect to the horizontal plane of the base 401. It is understood that other angles or inclinations of disc 402 can be utilized.

In use, the disc 402 moves between the closed position shown in full lines to an open position shown in broken lines in FIG. 12. An increase in the pressure of blood on the inlet or proximal side of the disc initially raises disc 402 off the proximal pivots 422 and 424, shown by broken lines. Disc 402 angularly moves upwardly and outwardly to the open position. When disc 402 is in the open position, it is inclined at a slight angle, preferably 75°–80° with respect to the longitudinal axis of passage 404. Disc 402 is located laterally of the central axis of the longitudinal passage and allows central flow of blood through the passage. At the same time, blood flows on opposite sides of the disc. Disc 42 is free to rotate 360° about its central axis on the rod 417 as it opens and closes.

The pressure of blood on the proximal side of the disc is sufficient to overcome the magnetic force from permanent magnet 416 acting on the end 419. As the flow of blood through passage 404 subsides or decreases, the pressure of the blood drops and then reverses so that blood will flow in the reverse direction through passage 404. This reverse flow closes the valve disc 402. The magnet 416 is operable to close the valve during the period when the pressure drops, thereby minimize the amount of reverse flow of blood through passage 404 needed to move disc 402 to its closed position. The magnet 416 urges the disc 402 toward the end 419 since this is a greater mass of material. Thus, the magnet 416 functions to make the valve disc responsive to the pressure of blood flowing through passage 404. When there is a minimum amount of pressure, the magnet will move disc 402 toward the closed position and will close the disc.

Referring to FIGS. 14 and 15, there is shown the fifth heart valve of the invention indicated generally at 500 for controlling the flow of blood in a heart. Valve 500 has an annular housing or base 501 accommodating a moving valving member 502. Base 501 has a generally cylindrical annular inner wall 503 defining a passage or opening 504 allowing the flow of blood through the valve base. Valving member 502 is movably positioned within passage 504 to permit one-way flow of blood through the passage and restrict the flow of blood in the reverse or opposite direction through passage 504.

Base 501 has a proximal annular flange 506 and a distal annular flange 507. Flanges 506 and 507 project laterally in an outward direction. A cylindrical outside wall 508 extends between the flanges 506 and 507 to provide an annular outwardly open groove for accommodating a suturing member. The suturing member may be suturing member 21 shown in FIGG. 2 or the suturing member shown in U.S. Pat. No. 3,781,969. Other types of suturing members can be mounted on base 501.

Valving member 502 is a disc having a generally flat, circular configuration and a circumferentially uninterrupted outer peripheral edge 509. Edge 509 -cooperates with portions of the inner wall 503 to restrict or limit reverse flow of blood through passage 504 when the disc 502 is in the closed position. As shown in FIG. 15, the diameter of disc 502 is such that the outer peripheral edge 503 is slightly spaced by annular space 511 from wall 503.

Sapce 511 is of a size to permit limited annular leakage or reverse flow of blood through passage 504 when the disc is in the closed position. The blood flows between the outer peripheral edge 509 and the adjacent inner wall 503 to wash the disc, pivot and wall surfaces and provide for continuous movement of the blood, thereby minimizing clot formation and regions of blood stagnation.

Disc 502 has a core or substrate 512 covered with a coat or skin 513. Skin 513 is a hard, wear-resistant material that is biologically inert and compatible with the material of the base. Preferably, skin 513 is a silicon-alloyed carbon material such as pyrolite carbon. The skin can be other material such as ceramic or plastic. The skin can have a plurality of layers as shown in FIG. 4. Substrate 512 can be any rigid material, as metal, plastic, carbon or the like. The substrate can have a hollow chamber or a number of chambers ro reduce its weight. Disc 502 can be made of metal, plastic or ceramic materials.

The center portion of disc 502 has a circular hole 514 defined with an inner circular wall 515. Wall 515 has a smooth, semi-circular cross sectional configuration whereby the inner circular wall 515 does not have any abrupt projections or edges that can interfere with the flow of blood through hole 514 or collect blood tissue.

Disc 502 is movably positioned in a free-floating relation in passage 504 with a retainer comprising a rod 517 and pivot means indicated generally at 521. The disc 502 has limited lateral movement, as shown in dotted lines in FIG. 15, and ...ited axial movement, as shown in broken lines, and is free to randomly rotate 360° about its central axis as it angularly moves between its open and closed positions.

An annular magnet 516 is located in substrate 512 around hole 514. Magnet 516 is covered with the skin 513. Magnet 516 is a permanent magnet and can be made of the same materials as magnet 416.

Rod 517 is integrally joined at 518 to a proximal or inflow portion of base 501. Rod 517 has a broad S or reverse curve shape. Preferably, rod 517 is an integral part of the base 501 and has been curved into the shape shown in FIG. 15. Rod 517 has a first section extended downwardly and then curved inwardly below the lower or proximal plane of the lower edge of base 501 to locate the first section 517A outside the passage 504. First section 517A is joined with a second section 517B extended upwardly through the hole 514 in disc 502. Section 517B terminates in an end section 519.

Sections 517B and 519 have an arcuate shape that generally follows the movement of the disc 502 as it moves between its open and closed positions. The circular cross section of end section 519 smaller than the cross section 517B. Referring to FIG. 16, the permanent magnet 516 is in close proximity to the section 517B when the disc 502 is in the closed position, as shown in full lines. When disc 512 is in the open position, as shown in broken lines, the permanent magnet 516 is adjacent the reduced diameter end 519 with major portions of the magnet being spaced a greater distance from the rod and thereby reduce the force exerted by magnet 516 to pull the disc 502 toward the rod and hold disc 502 open. Magnet 516 has sufficient force so that it is attracted to the larger portion 517B, thereby establishing a force which urges the disc 502 to its closed position. When the disc 502 is in the open position, as shown in broken lines in FIGS. 15 and 16, the circular cross section of end portion 519 is substantially smaller than the diameter of hole 514. This allows a limited amount of blood to flow through the hole and permits the disc 502 to have limited lateral movement and random rotational movement relative to the rod 517 and base 501.

As shown in FIGS. 14 and 15, disc 502 has an off-center pivotal movement so that when the disc is in the open position, the blood has unrestricted centralized flow through passage 504. Also, the blood flows adjacent opposite surfaces of disc 52, thereby washing both surfaces of the disc. Disc 502 pivots in a chordal region between its outer peripheral edge and its diameter.

Pivot means indicated generally at 521 cooperate with rod 517 to control the pivotal movement of the disc. The pivot means comprises a first pair of pivots 522 and 523 and a second pair of pivots 524 and 525. The first pair of pivots includes the proximal pivot 522 extended adjacent a proximal portion of the disc and into passage 504. The distal pivot 523 is located adjacent the top of the disc and extends into passage 504. Pivots 522 and 523 are integral with the base and have fulcrum surfaces which coact with portions of the disc to guide the disc and limit the open position of the disc, as shown in broken lines in FIG. 15. When the disc is in the open position, it is preferably at an angle of 75°–80° with respect to the longitudinal axis of the passage.

The pivots 522, 523, 524 and 525 are projections, elements or legs spaced from each other and extended into the passage. The pivots are located offcenter or in an eccentric location relative to the diameter of the passage whereby the disc 502 pivots about an offcenter or eccentric axis as it opens and closes. The pivot axis generally follows a chordal region of the passage and can shift relative to the diameter of the passage as the disc 502 opens and closes. In other words, the disc has limited lateral movement allowed by the size of the disc and the size of the hole relative to the diameter of the rod 514. The base 501 has an abutment or stop projection 526 located in general vertical alignment with the rod 517. Stop projection 526 has a top portion or face 527 adapted to be engaged by disc 502 when the disc is in the closed position. Face 527 in concert with the proximal pivots 522 and 524 holds the disc in an inclined position, as shown in FIG. 15, when the disc is in its closed position. Preferably, the inclination is 18° with respect to the horizontal plane of base 501. It is understood that other angles of inclination can be used for disc 502.

In use, with disc 502 in the closed position, as shown in full lines in FIG. 15, it will initially move upwardly or axially to the dotted line position until the distal or upper surface of the disc contacts the distal pivots 523 and 525. Disc 502 then will move around the fulcrum surfaces of the pivots 523 and 525 about an offcenter axis. Disc 502 will generally follow the curvature of rord 517. The force of the blood on the disc is sufficient to overcome the force of permanent magnet 516. Disc 502 also moves with the flowing blood so that the lower portion of the center hole of the disc engages the outer end 519 of the rod 517. This is shown in broken lines in FIG. 15. With the disc in the full open position, opposite portions of disc 502 engage the pairs of pivots 522, 523, 524 and 525 to hold the disc in a slight inclined position relative to the longitudinal axis of passage 504. The disc at all times is free to randomly rotate 360° about its central axis as it moves between its open and closed positions.

On the reduction in the pressure of the blood on the proximal side of disc 502 and the reduction of the flow of blood through the passage 504, the force of magnet 516 will initially move the disc 502 back in the direction toward the closed position. The magnetic force increases as the diameter of the rod section 517B increases. Thus, after the disc 502 is initially moved, it will increase its rate of movement to the closed position. The magnet 516 makes the closing of disc 502 responsive to the drop in pressure of the blood in a forward direction through the valve passage 504. When the flow of blood is nominal or in the transient stage between forward and reverse, the disc will be moving in the closed position because of the magnet. This minimizes the amount of reverse flow necessary to completely close the disc 502.

The heart valve and suturing member has been shown and described with respect to preferred embodiments thereof. Changes, modifications and substitutions of materials, structures, and sizes may be made by those skilled in the art without departing from the spirit of the invention.

The embodiments of the invention in which an exclusive property or privilege is claimed are defined as follows:

1. A heart valve prosthesis for controlling the flow of blood in a heart comprising: a base having an inner annular wall surrounding a passage for carrying blood through the base; disc means movable relative to said passage to an open position to allow flow of blood through said passage in one direction and to a closed position to restrict the flow of blood in the opposite direction through said passage, said disc means being free to rotate about its central axis as the disc means moves between its open and closed positions, said disc means having a hole through the central portion thereof and an annular uninterrupted outer peripheral edge cooperating with the base to restrict the flow of blood in the opposite direction through said passage when the disc means is in the closed position, means for holding the disc means in movable assembled relation with the base whereby the disc means is free to rotate about its central axis and is located off-center when in the open position allowing centralized flow of blood through the passage and flow of blood on opposite sides of the disc means, said means for holding the disc means including a rod having a section extended through the hole in the disc means, and means within the disc means cooperating with the means for holding the disc means for progressively moving the disc means from the open position to the closed position in response to a reduction of the pressure of blood moving through said passage.

2. The heart valve of claim 1 wherein: said means for holding the disc means includes pivot means on the base off-set from a diameter of the passage and engageable with the disc means for controlling the pivotal movement of the disc means off-center from a diameter of the disc means.

3. The heart valve of claim 1 wherein: said rod is secured to an in-flow portion of the base, said section projected in the downstream direction into the passage.

4. The heart valve of claim 1 wherein: said rod is secured to an in-flow portion of the base and has a general reverse curve shape and extends in a general radial plane relative to the passage, said section projected in the downstream direction into the passage.

5. The heart valve of claim 4 wherein: said means for holding the disc means includes pivot means on the base offset from a diameter of the passage and engageable with the disc means for controlling the pivotal movement of the disc means off-center from a diameter of the disc means.

6. The heart valve of claim 1 wherein: said rod is secured to an out-flow portion of the base, said section projected in the upstream direction into the passage.

7. The heart valve of claim 1 wherein: said outer peripheral edge of said disc means is spaced from the inner wall of the base when the disc means is in the closed position whereby limited reverse flow of blood is permitted through said passage.

8. The heart valve of claim 1 wherein: said means for holding the disc means includes means cooperating with the disc means to hold the disc means in an inclined position relative to the transverse plane of the passage when the disc means is in the closed position.

9. The heart valve of claim 1 wherein: said retaining means comprises a single rod having a base portion secured to the base and said section being a curved radially inwardly directed portion having an end projected through the hole in the disc means, said curved portion of said rod having a curvature that generally follows the pivotal path of the center hole in the disc means.

10. The heart valve of claim 9 including: means on the end of said rod to restrict reverse flow of blood through the hole in the disc when the disc is in the closed position.

11. The heart valve of claim 1 wherein: the section of the rod has a cross sectional size smaller than the size of the hole in the disc means whereby blood can flow through said hole.

12. The heart valve of claim 1 wherein: said disc means has an outer skin of pyrolite carbon.

13. The heart valve of claim 2 wherein: said base means and pivot means have outer skins of pyrolite carbon.

14. The heart valve of claim 1 wherein: the means for moving the disc means includes magnet means located within the disc means, said magnet means cooperating with the means for holding the disc means to move the disc means from the open position to the closed position.

15. The heart valve of claim 14 wherein: the magnet means includes an annular permanent magnet located around said hole.

16. The heart valve of claim 15 wherein: the section of the rod has an enlarged portion adjacent the disc means when the disc means is in the closed position.

17. A heart valve prosthesis for controlling the flow of blood in a heart comprising: a base having a passage for carrying blood through the base and means for accommodating a suturing member used to secure the heart valve to heart tissue, valving means movable relative to the base to an open position to allow blood to flow through the passage in one direction and to a closed position to restrict the flow of blood in the opposite direction through the passage, means for holding the valving means in movable assembled relation with the base, and means associated with the valving means and means for holding the valving means for progressively moving the valving means from the open position to the closed position in response to a reduction of the pressure of the blood moving through said passage.

18. The heart valve of claim 17 wherein: the means for moving the valving means includes magnet means associated with the valving means.

19. The heart valve of claim 17 wherein: the valving means is a disc having a center hole, said means for holding the valving means including a rod having a section extended through the hole.

20. The heart valve of claim 19 wherein: the means for moving the valving means includes magnet means located in the disc adjacent and around the hole, said magnet means cooperating with the rod for moving the disc from the open position to the closed position.

21. The heart valve of claim 20 wherein: the magnet means is a permanent magnet.

22. The heart valve of claim 20 wherein: the disc has a substrate and an outer skin covering the substrate, said magnet means being located under said skin.

23. The heart valve of claim 19 wherein: the section of said rod has an enlarged portion located in said hole when the disc means is in the closed position.

24. The heart valve of claim 19 wherein: said rod is secured to the in-flow side of the base, said section projected in the downstream direction into the passage.

25. The heart valve of claim 24 wherein: said rod has a generally reverse curve shape.

26. The heart valve of claim 17 wherein: the valving means is a disc.

27. The heart valve of claim 26 wherein: the means for holding the valving means includes pivot means on the base offset from the diameter of the passage and engageable with the disc means for controlling the movement of the valving means.

* * * * *